United States Patent [19]

Coke

[11] Patent Number: 5,534,434
[45] Date of Patent: *Jul. 9, 1996

[54] BASAL NUTRIENT MEDIUM FOR IN VITRO CULTURES OF LOBLOLLY PINES

[75] Inventor: Jay E. Coke, Summerville, S.C.

[73] Assignee: Westvaco Corporation, New York, N.Y.

[ * ] Notice: The term of this patent shall not extend beyond the expiration date of Pat. No. 5,534,433.

[21] Appl. No.: 457,026

[22] Filed: Jun. 2, 1995

[51] Int. Cl.$^6$ ........................................................ L12N 5/02
[52] U.S. Cl. ................................ 435/240.54; 435/240.4; 435/240.45
[58] Field of Search ........................... 435/240.4, 240.54, 435/240.45

[56] References Cited

U.S. PATENT DOCUMENTS 5,413,930  5/1995  Becwar et al. ...................... 435/240.4

FOREIGN PATENT DOCUMENTS

WO92/07460  5/1992  WIPO .

OTHER PUBLICATIONS

Webb, D. T., and O. D. Santiago. Cytokinin induced bud formation on carribean pine (*Pinus caribaea* Morlet) embryos in vitro. *Plant Science Letters* 32:17–21, 1983.

Abdullah, A. A., M. M. Yeoman, and J. Grace. In vitro adventitious shoot formation from embryonic and cotyledonary tissues of *Pinus brutia* Ten. *Plant Cell, tissue and Organ Culture* 5:35–44, 1985.

Aitken–Christie, J., A. P. Singh, and H. Davies. Multiplication of meristematic tissue – A new tissue culture system for radiata pine. In Proceedings of Genetic Manipulation of Woody Plants. Edited by J. Hanover and D. Keathley. *Plenum Press*. New York. p. 413–432, 1987.

Becwar, M. R., R. Nagnami, and S. R. Wann. Initiation of embryogenic cultures and somatic embryo development in loblolly pine (*Pinus taeda*). *Canadian Journal of Forest Research* 20:810–817, 1990.

Bornman, C. H. In vitro regeneration potential of the conifer phyllomorph. In Symposium on Clonal Forestry. Edited by G. Eriksson and K. Lendkvist. Swedish University of Agricultural Sciences, Department of Forest Genetics, Uppsala, Sweden. Research Notes 32. pp. 43–56, 1981.

Bornman, C. H. Possibilites and constraints in the regeneraton of trees from cotyledonary needles of *Picea abies* in vitro. *Physiologia Plantarum* 57:5–16, 1983.

Chesick, E. E., and M. R. Becwar. Effects of medium components on initiation of embryogenic cultures from loblolly pine immature zygotic embryos. Westvaco Forest Science Laboratory, Genetics and Biotechnology Center, Summerville, South Carolina. Research Report No. 126, 1992.

Gamborg, O. L., T. Murashige, T. A. Thorpe, and I. K. Vasil. Plant tissue culture media. In vitro 12:473–478, 1976.

Gresshoff, P. M. and C. H. Doy. Development and differentiation of haploid *Lycopercicon esculentum* (tomato). *Planta* 107:161–170, 1972.

Harry, I. S., C. Y. Lu, K. K. Sharma, and T. A. Thorpe. Micropropagation of western hemlock (*Tsuga heterophylla* [Raf.]Sarg.) from embryonic explants. *New Forests* 8:1–13, 1994.

Lin, Y., M. R. Wagner, and L. J. Heidmann. In vitro formaton of axillary buds by immature shoots of Ponderosa pine. *Plant Cell, Tissue and Organ Culture* 26:161–166, 1991.

Litvay, J. D., M. A. Johnson, D. Verma, D. Einspahr, and K. Weyrauch. Conifer suspension culture medium development using analytical data from developing seeds. *Institute of Paper Chemistry Technical Paper Series* 115:1–17, 1981.

Mehra–Palta, A., R. H. Smeltzer, and R. L. Mott. Hormonal control of induced organogenesis: Experiments with excised plant parts of loblolly pine. *Tappi* 61:37–40, 1978.

Mott, R. L. and H. V. Amerson. A tissue culture process for the clonal production of loblolly pine plantlets. North Carolina Agricultural Research Service, Technical Bulletin No. 271, 1981.

Mohammed, G. H., D. I. Dunstan, and T. A. Thorpe. Influence of nutrient medium upon shoot initiation on vegetative explants excised from 15– to 18 –year–old *Picea glauca*. *New Zealand Journal of Forestry Science* 16:297–305, 1986.

Murashige, T., and F. Skoog. A revised medium for rapid growth and bioassays with tobacco tissue culture. *Physiologia Plantarum* 15:473–497, 1962.

Neuman, P. R., F. Fong, R. J. Newton, and S. Sen. Induction of peroxidase isozymes during shoot enhancement by ABA in cotyledons explants of loblolly pine (*Pinus taeda* L.). *Journal of Plant Physiology* 139:343–349, 1992.

Schenk, R. U. and A. C. Hildebrandt. Medium and techniques for induction and growth of monocotyledonous and dicotyledonous plant cell cultures. *Canadian Journal of Botany* 50:199–204, 1972.

Tuskan, G. A., W. A. Sargent, T. Rensema, and J. A. Walla. Influence of plant growth regulators, basal media and carbohydrate levels on the in vitro development of *Pinus ponderosa* (Dougl. ex law.) cotyledon explants. *Plant Cell, Tissue and Organ Culture* 20:47–52, 1990.

Primary Examiner—David M. Naff
Assistant Examiner—L. Blaine Lankford
Attorney, Agent, or Firm—Daniel B. Reece, IV; Terry B. McDaniel; Richard L. Schmalz

[57] ABSTRACT

A basal nutrient culture medium for the in vitro culture of *Pinus taeda*, loblolly pine, is disclosed. The medium contains nitrate, ammonium, potassium, phosphorate, calcium, magnesium, sulfate, chlorine, sodium, borate, manganese, iron, zinc, copper, iodine, molybdenum oxide, cobalt, thiamine and EDTA.

20 Claims, No Drawings

1

BASAL NUTRIENT MEDIUM FOR IN VITRO CULTURES OF LOBLOLLY PINES

FIELD OF INVENTION

This invention relates to methods and materials for enhancing in vitro cultures of *Pinus taeda* L., or loblolly pine. In particular, this invention relates to novel aqueous media formulations of basal nutrients which promote optimal in vitro responses in tissue cultures of loblolly pine.

BACKGROUND OF THE INVENTION

Tissue culture methods are powerful tools which provide means to vegetatively propagate genetically superior plants of many species. Such methods have also been useful in a number of special applications, including rejuvenation of mature plant material, virus elimination, and genetic transformation. Of the various components of a tissue culture method, the basal nutrient medium is one of the most important factors influencing the success of culturing plant material in vitro (Gamborg et al. 1976).

As the nutrient medium is an essential part of tissue culture methods, it is not surprising that a number of different aqueous nutrient medium formulations have been taught in published reports on conifer tissue cultures. Many of these reports describe the use of aqueous nutrient media initially developed for use with other species. For example, MS (Murashige and Skoog 1962), SH (Schenk and Hildebrandt 1972), and GD (Gresshoff and Doy 1972) media were developed for use with angiosperms, but have been used for the tissue culture of *Pinus ponderosa* Dougl. ex Law. (Tuskan et al. 1990, Lin et al. 1991), *Pinus caribaea* Morlet (Webb and Santiago 1983), and *Pinus taeda* L. (Neuman et al. 1992). In various conifer tissue culture reports, several previously published medium formulations were screened and the one eliciting the best responses was chosen for subsequent use (Bornman 1983, Abdullah et al. 1985); while in other reports, various dilutions of published media were tested (Mott and Amerson 1981, Harry et al. 1994). Despite numerous attempts, the efforts to develop tissue culture methods for utilization with loblolly pine (*Pinus taeda* L.), have met with only limited success.

A number of aqueous basal nutrient media which are commonly used in tissue culture methods for various conifer species were evaluated specifically for use with loblolly pine. These basal media included $GD_{mod}$ medium (Mehra-Palta et al. 1978), $LMG_{20}$ medium (Mott et al. 1986), LP medium (Aitken-Christie et al. 1987), SH medium (Schenk and Hildebrandt 1972), and DCR medium (Becwar et al. 1990).

The $GD_{mod}$, $LMG_{20}$, LP, and SH media were tested for axillary shoot micropropagation and shoot culturing using several loblolly pine families. In this evaluation, significant problems were associated with the use of each of these basal media. Of the four media, SH medium was the least successful. Only a low percentage of the explants initially cultured on SH medium resulted in the development of axillary shoots, and very few of these axillary shoots lived long enough to give rise to additional new shoots. Many shoots on SH medium suffered from necrosis of the shoot tip, which eventually led to the death of the entire shoot. As few genotypes survived on SH medium for an entire year, this medium had the lowest percentage of surviving explants and the lowest overall production of axillary shoots of the four media tested. Survival was better on LP medium, but certainly not optimal. Only 43% of the explants responded with axillary shoots. Many of these resulting shoots also suffered from necrosis of the shoot tip, which eventually led to the death of the entire shoot. Survival was highest on $GD_{mod}$ and $LMG_{20}$ media (64% and 69% respectively) but the resulting shoots exhibited undesirable mature characteristics. The overall rate of in vitro shoot growth and the response to root-induction treatments were significantly lower for shoots from GD and $LMG_{20}$ media than for shoots from LP medium. To summarize: when utilized in tissue culture methods for loblolly pine shoots, none of these published nutrient media achieved the desired results of high survival rates, good shoot production, and enhancement of juvenile characteristics (such as rapid sustained shoot growth and high rooting potential).

Several published basal media were also evaluated for their effect on somatic embryogenesis using several loblolly pine families (Chesick and Becwar 1992). Immature megagametophytes containing zygotic embryos at a developmental stage previously determined to be responsive (Becwar et al. 1990) were cultured, and data on the extruding embryogenic tissue were collected. Overall, DCR and SH media resulted in highest frequencies of extrusion and proliferation of embryogenic tissue. Despite this ranking, the frequency of embryogenic tissue extrusion and proliferation was low. Initial extrusion percentages averaged 30% for SH and 28% for DCR. Moreover, the percentage of cultures which continued to proliferate declined rapidly, and by nine weeks averaged only 11% for SH and 7% for DCR. To summarize: none of these published nutrient media resulted in the survival of a large percentage of responding cultures for loblolly pine somatic embryogenesis.

Therefore, the object of the present invention is to provide an effective aqueous basal nutrient media for in vitro tissue cultures of loblolly pine.

SUMMARY OF THE INVENTION

This objective is met by the present invention, which utilizes a unique combination of basal nutrients and concentrations to promote optimal in vitro responses in loblolly pine tissue cultures. This aqueous basal nutrient medium (when combined with other factors such as an appropriate carbohydrate source, growth regulators, activated carbon, etc.) provides the basic nutrients suitable for numerous tissue culture applications. Such applications include the in vitro culture of loblolly pine cells, tissues, and organs (from both juvenile and mature sources) for the purposes of asexual propagation, rejuvenation, virus elimination, and genetic transformation.

DESCRIPTION OF THE PREFERRED EMBODIMENT

The present invention alleviates deficiencies and problems associated with prior art culture media by providing an aqueous basal media which is reliable and efficient to use with loblolly pine tissue cultures. The invention media consists of the unique combination and concentrations of nutrients listed in Table I below.

TABLE I

Nutrient Components And Concentrations Of Basal Nutrient Medium.

| Medium component | Concentration (millimolar or mM) |
|---|---|
| $NO_3$ | 8–30 |
| L-Glutamine | 6–18 |
| K | 10–25 |
| $H_2PO_4$ | 1.0–2.3 |
| Ca | 2–7 |
| Mg | 1–9 |
| $SO_4$ | 1–10 |
| Cl | .0001–25 |
| Na | .1–.3 |
| $H_2BO_4$ | .05–.6 |
| Mn | 0.124–.45 |
| Fe | .05–.2 |
| Zn | .015–.2 |
| Cu | .0005–.003 |
| I | .0001–.001 |
| $MoO_4$ | .00005–.006 |
| Co | .00005–.006 |
| Thiamine | .0002–.002 |
| *EDTA | .05–.2 |

*EDTA = ethylenediaminetetraacetic acid.

The preferred combination and concentrations of nutrients for the aqueous basal media is listed in Table II below.

TABLE II

Preferred Nutrient Components And Concentrations of Basal Nutrient Medium.

| Medium component | Concentration (mM) |
|---|---|
| $NO_3$ | 9–24.9 |
| L-Glutamine | 6.9–15.7 |
| K | 13.6–19.8 |
| $H_2PO_4$ | 1.5–2.1 |
| Ca | .15–5.08 |
| Mg | 1.46–7.75 |
| $SO_4$ | 1.68–8 |
| Cl | .000105–20.4 |
| Na | .224–.232 |
| $H_2BO_4$ | .1–.5 |
| Mn | .09–.124 |
| Fe | .1–.15 |
| Zn | .03–.15 |
| Cu | .001–.002 |
| I | .0002–.0008 |
| $MoO_4$ | .000103–.00517 |
| Co | .000105–.000549 |
| Thiamine | .0003–.00119 |
| EDTA | .1–1.5 |

The media may include any of the additional nutrients and/or additives commonly utilized in tissue culture media, including: carbohydrates, hormones, amino acids, vitamins, activated carbon, minerals, pH buffers, gelling agents, and the like.

The basal nutrient medium contains the many elements essential to plant growth at concentrations appropriate for loblolly pine. However, the basal media may be supplemented with specific growth regulators to achieve various developmental responses, including embryogenesis, adventitious and axillary shoot development, and rooting.

The following examples are provided to further illustrate the present invention and are not to be construed as limiting the invention in any manner.

EXAMPLE 1

The following Example evaluated three different formulations of the invention aqueous basal nutrient media (hereafter referred to as WV1, WV2, and WV3 basal media) against two commonly known and used aqueous basal media formulations—$LMG_{20}$ (Mott et al. 1987) and LP (Aitken-Christie et al. 1987)—for their influences on in vitro micropropagation and shoot culturing of loblolly pine. The respective aqueous basal media formulations are listed in Table III below:

TABLE III

Basal Nutrient Media Evaluations For In Vitro Micropropagation And Shoot Culture Of Loblolly Pine.

| Component | Improved Media (concentration/mM) | | | Published Media (concentration/mM) | |
|---|---|---|---|---|---|
| | WV1 | WV2 | WV3 | $LMG_{20}$ | LP |
| $NO_3$ | 24.9 | 16.9 | 9.0 | 1.0 | 33 |
| $NH_4$ | — | — | — | — | 5 |
| L-Glutamine | 6.9 | 11.3 | 15.7 | 20.0 | — |
| K | 19.8 | 19.8 | 19.8 | 13.6 | 19.8 |
| $PO_4$ | 2.0 | 2.0 | 2.0 | 2.5 | 2.0 |
| Ca | 4.08 | 4.08 | 4.08 | 0.15 | 5.08 |
| Mg | 7.75 | 7.75 | 7.75 | 7.75 | 1.46 |
| $SO_4$ | 7.87 | 7.87 | 7.87 | 8.00 | 1.68 |
| Cl | 1.10 | 9.10 | 17.0 | 10.40 | .000105 |
| Na | 0.224 | 0.224 | 0.224 | 0.232 | 0.224 |
| $H_2BO_4$ | 0.500 | 0.500 | 0.500 | 0.500 | 0.100 |
| Mn | 0.090 | 0.090 | 0.090 | 0.124 | 0.090 |
| Fe | 0.100 | 0.100 | 0.100 | 0.100 | 0.100 |
| Zn | 0.030 | 0.030 | 0.030 | 0.150 | 0.030 |
| Cu | 0.001 | 0.001 | 0.001 | 0.002 | 0.001 |
| I | 0.00048 | 0.00048 | 0.00048 | 0.02500 | 0.00048 |
| $MoO_4$ | 0.00103 | 0.00103 | 0.00103 | 0.00517 | 0.00103 |
| Co | 0.000105 | 0.000105 | 0.000105 | 0.000549 | 0.000105 |
| Thiamine | 0.00119 | 0.00119 | 0.00119 | 0.00030 | 0.00119 |
| Myoinositol | 5.55 | 5.55 | 5.55 | 0.55 | 5.55 |
| EDTA | 0.111 | 0.111 | 0.111 | 0.111 | 0.111 |

In this example, the basal nutrient media were prepared with the addition of a similar quantity of sucrose (20 g/l), activated carbon (5 g/l), and gelling agent (8 g/l agar). Plant growth regulators were not included in any of the media. Seedling shoot sections were cultured on each of the media, and subcultured to fresh media at eight-week intervals. New axillary shoots were excised upon reaching at least 2.0 cm in length, and cultured independently. Approximately six months after initiating the original cultures, a sample of axillary shoots from each medium and family were evaluated for rooting under greenhouse conditions.

Specifically, in this example seedlings from each of eight loblolly pine families were grown under greenhouse conditions for ten weeks. Epicotyls from the ten-week-old seedlings of each family were excised, and the stems were shortened to 3.0 cm by removing the shoot base. These shoots were washed for five minutes with liquid dishwashing soap, and then surface sterilized for 30 seconds in a 70% ethanol solution followed by five minutes in a 20% solution of household bleach (1.05% sodium hypochlorite) containing four drops per liter TWEEN 20 surfactant. After the surface sterilization treatment, the shoots were rinsed three times with sterile water and stored in a laminar flow hood until use.

Under aseptic conditions, the shoot apex of each epicotyl was removed by severing the stem at the point where the most distal needles come together and the stem becomes visible. Each decapitated shoot was then trimmed to approximately 2.5 cm of visible stem by removing the base of the shoot damaged during surface sterilization. Each prepared 2.5 cm shoot section was then placed in culture by inserting the base approximately 1.0 cm into the nutrient medium contained in test tubes. For each family, one explant per tube and 45 tubes per test medium were initiated. The cultures were then randomized and incubated for eight weeks at 25° C., under a 16 hr/day photoperiod of approximately 60 $uE \cdot s^{-1} \cdot m^{-2}$ light from VITA-LITE fluorescent bulbs.

At eight-week intervals, all axillary shoots with at least 2.0 cm of visible stem were excised from the original explants and other resulting shoot sections. The excised shoots were divided into 2.0 cm sections and the resulting shoots and shoot sections were cultured in test tubes containing fresh test medium as before. Cultures were incubated as before.

After 24 weeks from when the original epicotyls were cultured, the number of axillary shoots with at least 2.0 cm of visible stem and an intact apex was recorded for each genotype. Data were also collected on the number of shoots with fascicular needles, the number of shoots with terminal bud development, and the amount of shoot growth occurring over an eight-week period.

At 24 weeks from initiation, after recording the above data, a random sample of axillary shoots from each medium was selected for each family to evaluate the rooting potential of the shoots. The shoots were shortened to 2.0 cm by removing the shoot bases and the basal 0.5 cm of each shoot was immediately dipped in a 1000 mg/liter Indole-butyric acid solution prepared with 50% ethanol. The base of each shoot was then inserted 1.0 cm deep into a 1:1 (by volume) perlite:vermiculite mix contained in flats. The shoots were incubated in a greenhouse for 10 weeks under intermittent mist and approximately 50% shade. The rooting medium temperature was targeted at 27° C. At the end of 10 weeks, the number rooted shoots was recorded. A sample of the rooted shoots originating from each in vitro nutrient medium was planted in pots and grown for several months under greenhouse conditions. The evaluation results are listed in Table IV below.

TABLE IV

Evaluation of Basal Nutrients For In Vitro Micropropagation And Shoot Culture Of Loblolly Pine.
Means were calculated across eight families.

|  | Improved Media | | | Published Media | |
|---|---|---|---|---|---|
|  | WV1 | WV2 | WV3 | LMG$_{20}$ | LP |
| % Explants surviving to produce axil. shoots | 62 | 73 | 81 | 36 | 28 |
| Avg. axil. shoot growth over 8 week period (mm) | 44 | 45 | 44 | 17 | 39 |
| % Rooted axil. shoots | 20 | 26 | 29 | 6 | 15 |
| Avg. length of primary needles (mm) | 38 | 42 | 42 | 26 | 33 |
| % Axil. shoots with fascicular needles | 22 | 27 | 39 | 85 | 31 |
| % Axil. shoots with terminal resting bud | 1 | 2 | 4 | 64 | 0 |

Several important aspects of in vitro shoot culture—including survival, shoot production, shoot growth, and rooting potential—were improved for loblolly pine when the different invention basal nutrient media were utilized. Improved rooting, as well as improved shoot growth, were partially a result of the enhanced juvenility that occurred in the shoots grown on these novel media formulations. Evidence of this desirable juvenile condition lies in the juvenile morphology exhibited by these shoots. As in most pine species, this juvenile morphology was characterized by longer primary needles, a less frequent occurrence of fascicular needles, and a near absence of resting, terminal buds.

The data in Table IV clearly indicate that the use of the invention aqueous basal nutrient media achieved overall superior results in explant survival, shoot production, shoot growth, and rooting in the micropropagating and culturing of shoots of loblolly pine when compared to the commonly-used, published media. Healthy, rooted loblolly pine plants resulted from the use of this invention.

EXAMPLE 2

The following Example evaluated an invention aqueous basal nutrient medium (WV3 basal media) against two commonly-used, published basal media formulations—SH (Schenk and Hildebrandt 1972) and DCR (Becwar et al. 1990)—for their influences on the initiation of somatic embryogenesis in loblolly pine. The somatic embryogenesis method followed in this example is taught in commonly assigned U.S. Pat. No. 5,413,930 (which is hereby incorporated by reference). The respective aqueous basal media formulations are listed in Table V below:

TABLE V

Media Evaluation For Somatic Embryogenesis In Loblolly Pine

| Component | Improved nutrient concs. (mM) | Published media nutrient concentrations (mM) | |
|---|---|---|---|
|  | WV3 | SH | DCR |
| NH$_4$ | — | 2.6 | 5.0 |
| NO$_3$ | 9.0 | 24.8 | 10.8 |
| L-Glutamine | 15.7 | — | — |
| K | 19.8 | 24.8 | 4.7 |
| H$_2$PO$_4$ | 2.00 | 2.61 | 1.30 |
| Ca | 4.08 | 1.37 | 3.00 |
| Mg | 7.75 | 1.63 | 1.50 |
| SO$_4$ | 7.87 | 1.74 | 1.08 |
| Cl | 17.0 | 2.74 | 1.20 |
| Na | 0.224 | 0.120 | 0.220 |
| H$_2$BO$_4$ | 0.500 | 0.081 | 0.100 |
| Mn | 0.090 | 0.059 | 0.132 |
| Fe | 0.100 | 0.054 | 0.100 |
| Zn | 0.0300 | 0.0035 | 0.0300 |
| Cu | 0.0010 | 0.0008 | 0.0010 |
| I | 0.00048 | 0.00602 | 0.00500 |
| MoO$_4$ | 0.00103 | 0.00041 | 0.00100 |
| Co | 0.000105 | 0.000422 | 0.000110 |
| Ni | — | — | 0.00011 |
| Glycine | — | — | 0.0267 |
| Nicotinic acid | — | 0.04065 | 0.00406 |
| Pyridoxine | — | 0.00243 | 0.00243 |
| Thiamine | 0.00119 | 0.01484 | 0.00297 |
| EDTA | 0.111 | 0.059 | 0.111 |

In this Example, the nutrient media for embryogenic tissue initiation and proliferation were prepared with the addition of a similar quantity of sucrose (30 g/l), myo-inositol (500 mg/l), 2,4-dichlorophenoxyacetic acid (3 mg/l), N$^6$ benzyladenine (0.5 mg/l), casein hydrolysate (500 mg/l), and GELRITE (1.25 g/l). (GELRITE is a gellan gum manufactured by Merck, Inc.) The nutrient medium for embryo development consisted of the WV3 basal nutrients (Table V) with the addition of sucrose (30 g/l); myo-inositol (100 mg/l); maltose (60 g/l); polyethylene glycol 4000 (60 g/l); and GELRITE (2.0 g/l).

Megagametophytes from immature loblolly pine seeds were cultured on each of the media, and subcultured to fresh media at 7 and 10 weeks after culture initiation. Proliferating embryogenic tissue was removed from the original explants at week seven and cultured independently. After ten weeks, samples of proliferating tissue from several families initiated on the WV3 basal medium were transferred to embryo-development medium to assess the embyogenicity of these cultures.

Specifically, in this example immature cones containing seeds from six loblolly pine families were collected mid-July in Ravenal, S.C. After collection, the cones were stored at 4° C. in the dark for approximately five weeks. Seeds from several cones in each family were removed and pooled for each of the eight families, and stored overnight on moist filter paper in the refrigerator.

Seeds were then surface-sterilized in 10% household bleach (0.53% sodium hypochlorite) for 15 minutes, followed by three, 5-minute rinses in sterile water. Following sterilization, the seed coat, nucellus, and any other exterior tissues were aseptically removed from the megagametophytes. The megagametophyte explants were then placed horizontally on the three media contained in petri dishes (Table 4). Ninety-six explants were cultured on each medium (8 explants per petri dish). The petri dishes were then sealed with Parafilm and incubated in the dark at 23° C. for seven weeks. At the end of four and seven weeks, data were collected on the extrusion of proliferating embryogenic tissue from the micropylar end of the megagametophytes. At seven weeks, this proliferating embryogenic tissue was then transferred to fresh medium, identical to the initial culture. These new cultures were then incubated as described above for an additional three weeks. At ten weeks from culture initiation, data on the number of embryogenic cell lines continuing to proliferate were recorded for each medium. A sample of genotypes proliferating on WV3 medium was transferred to the embryo-development medium to assess the embryogenicity of these cultures. Tissue samples of these genotypes were transferred to fresh embryo-development medium every three weeks. After nine weeks on embryo-development medium, data on the number of cotyledonary stage embryos were collected for each of the genotypes sampled.

TABLE VI

Percentage Of Initially Cultured Genotypes With Proliferating Embryogenic Tissue (Means Calculated Across Six Families)

| Time in culture | Improved Media | Published Media | |
|---|---|---|---|
| | WV3 | SH | DCR |
| 4 weeks | 45 | 34 | 33 |
| 7 weeks | 23 | 16 | 13 |
| 10 weeks | 16 | 10 | 7 |

As the results in Table VI clearly indicate, the frequency of extrusion and proliferation of embryogenic tissue was improved for loblolly pine when the invention aqueous basal nutrient medium was utilized. Although the percentage of cultures extruded on WV3 medium declined somewhat over a ten-week period, the percentage of proliferating cultures remained higher than that of DCR and SH medium at ten weeks. Of the sample of genotypes transferred to embryo-development medium, 77% produced mature, cotyledonary stage somatic embryos. Among these responding genotypes, the number cotyledonary stage somatic embryos produced ranged from 1 to 145. The use of an invention basal nutrient medium resulted in a more successful initiation and proliferation of embryogenic tissue than that provided by commonly-used, published media for somatic embryogenesis of loblolly pine. Healthy, cotyledonary somatic embryos resulted from the use of this invention.

Many modifications and variations of the present invention will be apparent to one of ordinary skill in the art in light of the above teachings. It is therefore understood that the scope of the invention is not to be limited by the foregoing description, but rather is to be defined by the claims appended hereto.

BIBLIOGRAPHY

Abdullah, A. A., M. M. Yeoman, and J. Grace. 1985. In vitro adventitious shoot formation from embryonic and cotyledonary tissues of *Pinus brutia* Ten. Plant Cell, Tissue and Organ Culture 5:35–44.

Aitken-Christie, J., A. P. Singh, and H. Davies. 1987. Multiplication of meristematic tissue—A new tissue culture system for radiata pine. In Proceedings of Genetic Manipulation of Woody Plants. Edited by J. Hanover and D. Keathley. Plenum Press. New York. p. 413–432.

Becwar, M. R., R. Nagmani, and S. R. Wann. 1990. Initiation of embryogenic cultures and somatic embryo development in loblolly pine (*Pinus taeda*). Canadian Journal of Forest Research 20: 810–817.

Bornman, C. H. 1983. Possibilities and constraints in the regeneration of trees from cotyledonary needles of *Picea abies* in vitro. Physiologia Plantarum 57:5–16.

Chesick, E. E., and M. R. Becwar. 1992. Effects of medium components on initiation of embryogenic cultures from loblolly pine immature zygotic embryos. Westvaco Forest Science Laboratory, Genetics and Biotechnology Center, Summerville, S.C. Research Report No. 126.

Gamborg, O. L., T. Murashige, T. A. Thorpe, and I. K. Vasil. 1976. Plant tissue culture media. In Vitro 12:473–478.

Gresshoff, P. M. and C. H. Doy. 1972. Development and differentiation of haploid *Lycopercicon esculentum* (tomato). Planta 107: 161–170.

Harry, I. S., C. Y. Lu, K. K. Sharma, and T. A. Thorpe. 1994. Micropropagation of western hemlock (*Tsuga heterophylla* [Raf.]Sarg.) from embryonic explants. New Forests 8:1–13.

Lin, Y., M. R. Wagner, and L. J. Heidmann. 1991. In vitro formation of axillary buds by immature shoots of Ponderosa pine. Plant Cell, Tissue and Organ Culture 26:161–166.

Mehra-Palta, A., R. H. Smeltzer, and R. L. Mott. 1978. Hormonal control of induced organogenesis: Experiments with excised plant parts of loblolly pine. Tappi 61:37–40.

Mott, R. L. and H. V. Amerson. 1981. A tissue culture process for the clonal production of loblolly pine plantlets. North Carolina Agricultural Research Service, Technical Bulletin No. 271.

Mott, R. L., H. V. Amerson, and L. J. Frampton. 1986. Micropropagation. In 1987 Annual Progress Report— Special Project on Tissue Culture. Forest Biology Research Center/North Carolina Agriculture Research Service/North Carolina State University. p. 34–53.

Murashige, T., and F. Skoog. 1962. A revised medium for rapid growth and bioassays with tobacco tissue culture. Physiologia Plantarum 15: 473–497.

Neuman, P. R., F. Fong, R. J. Newton, and S. Sen. 1992. Induction of peroxidase isozymes during shoot enhancement by ABA in cotyledons explants of loblolly pine (*Pinus taeda* L.). Journal of Plant Physiology 139:343–349.

Schenk, R. U. and A. C. Hildebrandt. 1972. Medium and techniques for induction and growth of monocotyledonous and dicotyledonous plant cell cultures. Canadian Journal of Botany 50:199–204.

Tuskan, G. A., W. A. Sargent, T. Rensema, and J. A. Walla. 1990. Influence of plant growth regulators, basal media and carbohydrate levels on the in vitro development of *Pinus ponderosa* (Dougl. ex Law.) cotyledon explants. Plant Cell, Tissue and Organ Culture 20: 47–52.

Webb, D. T., and O. D. Santiago. 1983. Cytokinin induced bud formation on caribbean pine (*Pinus caribaea* Morlet) embryos in vitro. Plant Science Letters 32: 17–21.

What is claimed is:

1. An aqueous basal nutrient medium for loblolly pine tissue cultures which comprises: 8–30 mM of $NO_3$, 6–18 mM of L-glutamine, 10–25 mM of K, 1–2.3 mM of $H_2PO_4$, 2–7 mM of Ca, 1–9 mM of Mg, 1–10 mM of $SO_4$, 0.0001–25 mM of Cl, 0.1–0.3 mM of Na, 0.05–0.6 mM of $H_2BO_4$, 0.124–0.45 mM of Mn, 0.05–0.2 mM of Fe, 0.015–0.2 mM of Zn, 0.0005–0.003 mM of Cu, 0.0001–0.001 mM of I, 0.00005–0.006 mM of $MoO_4$, 0.00005–0.006 mM of Co, 0.0002–0.002 mM of thiamine, and 0.05–0.2 mM of ethylenediaminetetraacetic acid.

2. The aqueous basal nutrient medium of claim 1 wherein said $NO_3$ concentration is 9–24.9 mM.

3. The aqueous basal nutrient medium of claim 1 wherein said L-glutamine concentration is 6.9–15.7 mM.

4. The aqueous basal nutrient medium of claim 1 wherein said K concentration is 13.6–19.8 mM.

5. The aqueous basal nutrient medium of claim 1 wherein said $H_2PO_4$ concentration is 1.5–2.1 mM.

6. The aqueous basal nutrient medium of claim 1 wherein said Ca concentration is 0.15–5.08 mM.

7. The aqueous basal nutrient medium of claim 1 wherein said Mg concentration is 1.46–7.75 mM.

8. The aqueous basal nutrient medium of claim 1 wherein said $SO_4$ concentration is 1.68–8 mM.

9. The aqueous basal nutrient medium of claim 1 wherein said Cl concentration is 0.000105–20.4 mM.

10. The aqueous basal nutrient medium of claim 1 wherein said Na concentration is 0.224–0.232 mM.

11. The aqueous basal nutrient medium of claim 1 wherein said $H_2BO_4$ concentration is 0.1–0.5 mM.

12. The aqueous basal nutrient medium of claim 1 wherein said Mn concentration is 0.09–0.124 mM.

13. The aqueous basal nutrient medium of claim 1 wherein said Fe concentration is 0.1–0.15 mM.

14. The aqueous basal nutrient medium of claim 1 wherein said Zn concentration is 0.03–0.15 mM.

15. The aqueous basal nutrient medium of claim 1 wherein said Cu concentration is 0.001–0.002 mM.

16. The aqueous basal nutrient medium of claim 1 wherein said I concentration is 0.0002–0.0008 mM.

17. The aqueous basal nutrient medium of claim 1 wherein said $MoO_4$ concentration is 0.000103–0.00517 mM.

18. The aqueous basal nutrient medium of claim 1 wherein said Co concentration is 0.000105–0.000549 mM.

19. The aqueous basal nutrient medium of claim 1 wherein said thiamine concentration is 0.0003–0.00119 mM.

20. The aqueous basal nutrient medium of claim 1 wherein said ethylenediaminetetraacetic acid concentration is 0.1–1.5 mM.

* * * * *